United States Patent [19]
Knoth

[11] Patent Number: 5,405,409
[45] Date of Patent: Apr. 11, 1995

[54] HYDRAULIC CONTROL UNIT FOR PROSTHETIC LEG

[76] Inventor: Donald E. Knoth, 3035 Dryden Rd., Dayton, Ohio 45439

[21] Appl. No.: 185,586

[22] Filed: Jan. 21, 1994

Related U.S. Application Data

[63] Continuation of Ser. No. 993,678, Dec. 21, 1992.

[51] Int. Cl.[6] ............................ A61F 2/64; A61F 2/74
[52] U.S. Cl. ...................... 623/44; 188/314; 188/322.19; 267/129
[58] Field of Search ................ 623/44, 39, 43, 26; 188/311, 322.19, 314; 267/124, 129; 92/85 R, 85 B, 84, 110

[56] References Cited

U.S. PATENT DOCUMENTS

| | | | |
|---|---|---|---|
| 2,859,451 | 11/1958 | Mauch | 623/39 |
| 3,151,856 | 10/1964 | Bresk et al. | 267/129 |
| 5,092,902 | 3/1992 | Adams et al. | 623/44 X |

FOREIGN PATENT DOCUMENTS 0503775  9/1992  European Pat. Off. ............ 623/44

*Primary Examiner*—David H. Willse
*Attorney, Agent, or Firm*—Jacox & Meckstroth

[57] ABSTRACT

A prosthetic leg has a pivotal knee joint and a hydraulic fluid control unit connected to provide variable forces which dampen flexion and extension of the knee and also bias the leg to its extended position. The unit includes an aluminum housing lined with an axially adjustable sleeve and control bushing defining a cylindrical operating chamber which receives a piston mounted on a tubular piston rod. The housing and operating chamber receive hydraulic fluid or oil which flows during movement of the piston through fluid control ports, channels and adjustable gaps defined by the sleeve and bushing for damping the movement of the rod. The piston rod encloses a gas filled flexible bladder which forms an oil accumulator during inward movement of the piston rod into a displacement chamber and also produces variable forces for moving the piston rod outwardly to its extended position. An annular seal engages an inner portion of the piston rod and prevents the higher hydraulic pressure in the displacement chamber from transferring to the operating chamber and the annular seal between the housing and the outer portion of the piston rod.

18 Claims, 2 Drawing Sheets

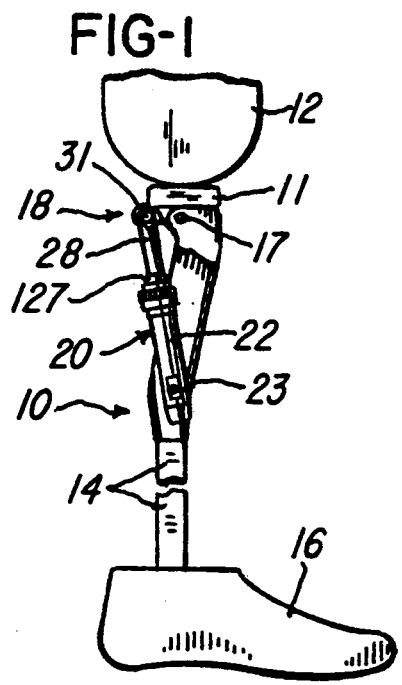
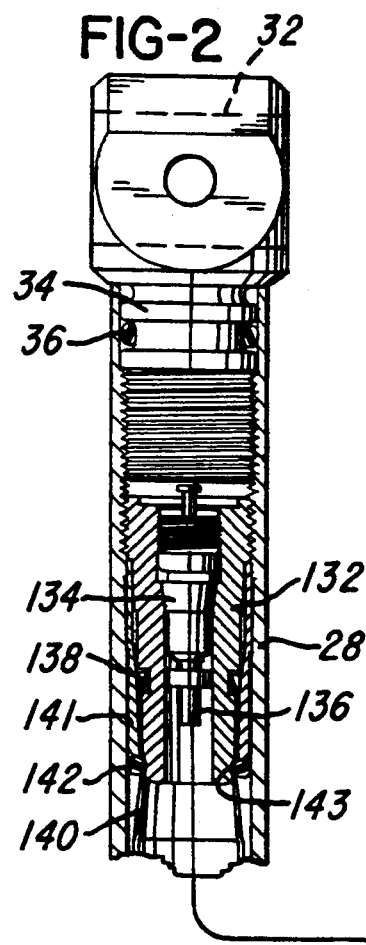
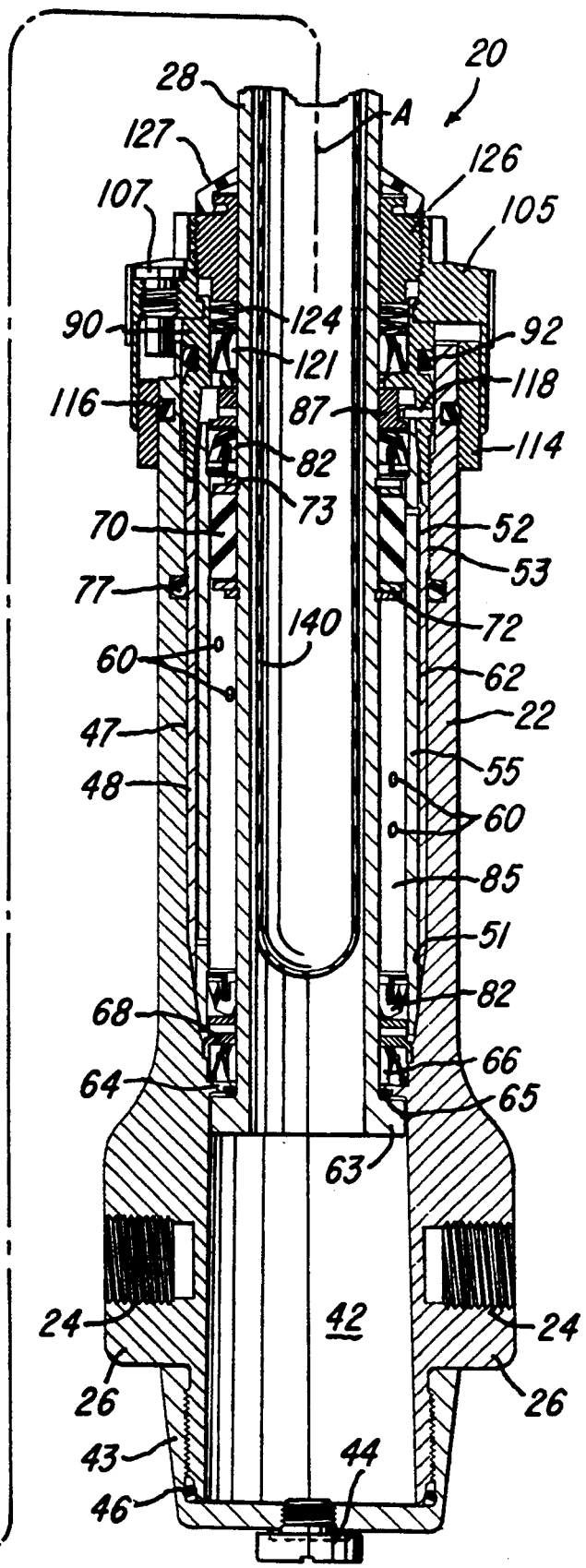

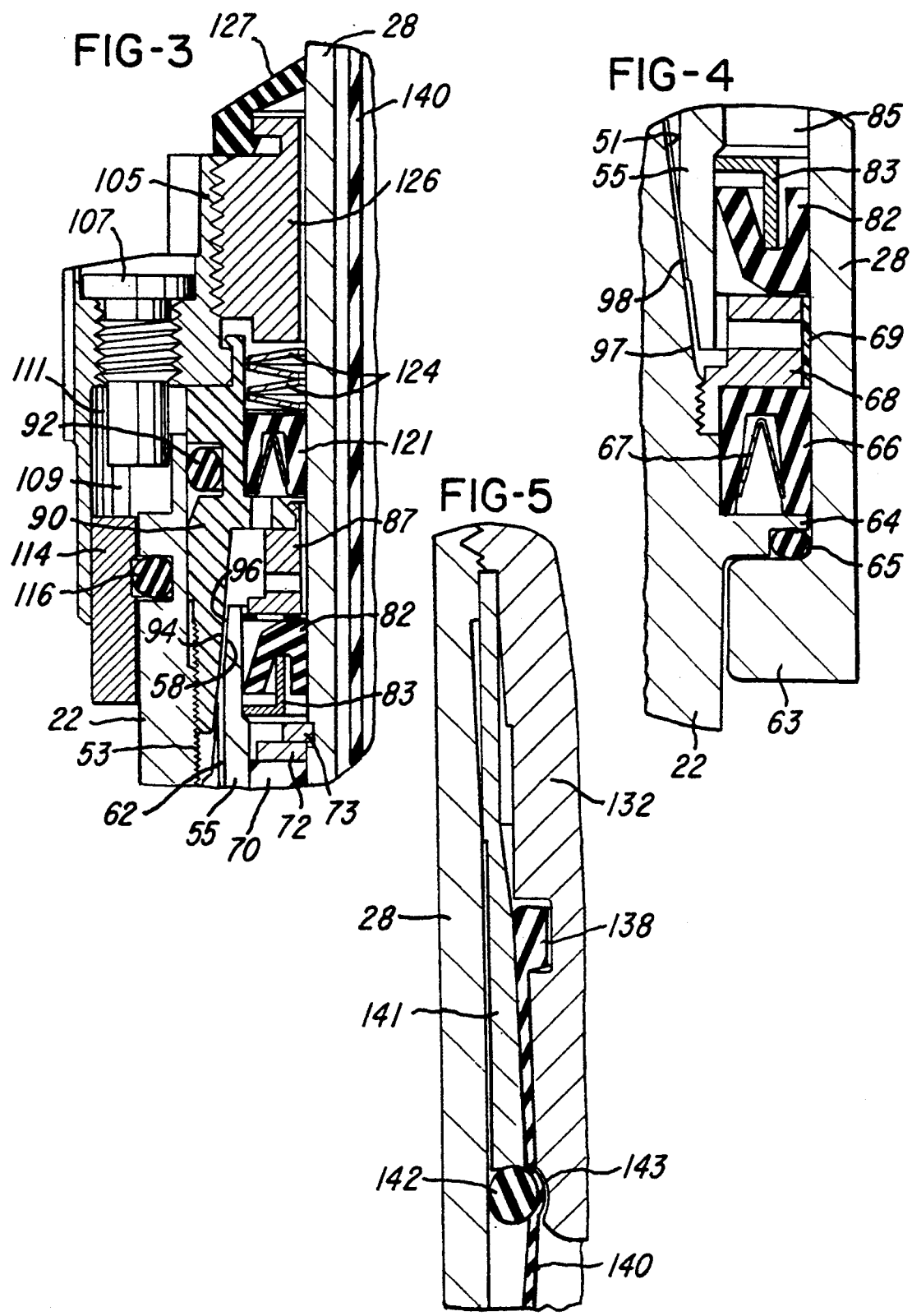

HYDRAULIC CONTROL UNIT FOR PROSTHETIC LEG

This application is a continuation of application Ser. No. 07/993,678, filed Dec. 21, 1992.

BACKGROUND OF THE INVENTION

In the art of hydraulic fluid control cylinders or units for use in a prosthetic leg at the knee joint, for example, as disclosed in U.S. Pat. No. 2,859,451 assigned to the Assignee of the present invention, it is desirable to minimize the size and weight of the unit while providing variable and adjustable damping forces or moments during flexion and extension of the knee and also variable biasing forces for moving the leg to its extended position. As disclosed in the above mentioned U.S. Pat. No. 2,859,451, the hydraulic control unit generally includes a housing which defines an oil reservoir, and a cylinder projects downwardly into the housing in spaced relation. The cylinder confines a control bushing which defines a staggered array of ports connected by corresponding axially extending channels to tapered passages or gaps at opposite ends of the bushing for controlling the oil flow when a piston and piston rod move axially within the bushing to produce variable damping forces. The bushing is axially adjustable within the cylinder for independently adjusting the tapered gaps according to the constant damping forces desired.

A hydraulic fluid control unit of the type disclosed in U.S. Pat. No. 2,859,451 has also been constructed by Applicants' Assignee with a coil compression spring located within the housing and surrounding the cylinder for engaging an annular seal and piston confined between the cylinder and housing. This spring and annular piston form an oil accumulator which receives the displaced hydraulic fluid when the piston rod is forced into the cylinder and housing. The spring biased annular piston also produce an increasing biasing force against the oil as the knee flexes and functions to urge the piston rod outwardly for returning the artificial leg to its extended or generally straight position. Other forms of hydraulic fluid control units for prosthetic legs are disclosed in U.S. Pat. Nos. 3,316,558, 4,065,815, 4,212,087, 4,578,082 and No. 4,595,179.

SUMMARY OF THE INVENTION

The present invention is directed to an improved hydraulic control unit for use with a knee joint of a prosthetic leg and which also produces variable forces to produce movement of the prosthetic leg simulating that of the natural leg over a wide range walking speeds. The control unit of the invention provides the desirable features and advantages of reduced size and weight, convenient adjustment of the variable biasing force applied to extend the prosthetic leg as well as convenient adjustment of the damping forces applied during flexion and extension of the knee. In addition, the control unit of the invention has fewer parts, is more economical in construction and more dependable in operation.

The above advantages are provided in a preferred embodiment of the invention wherein an aluminum tubular housing defines a hydraulic fluid or oil reservoir and holes for receiving pivot pins. The housing is lined with a cylindrical sleeve which tightly surrounds and cooperates with a cylindrical control bushing to define a staggered array of hydraulic control ports and axially extending channels or passages through which the oil flows to produce variable damping forces. A tubular piston rod extends through an operating chamber defined by the control bushing and into a displacement chamber. The piston rod supports a piston for sliding contact with the bushing. Annular one way check valves are supported at opposite ends of the operating chamber adjacent tapered annular flow control gaps, and the bushing and sleeve are adjustable axially within the housing for independently adjusting the gaps to select the desired constant damping forces which resist knee flexion and extension.

The tubular piston rod encloses an elongated flexible rubber-like bladder which is filled with a pressurized gas through a valve within the outer end portion of the rod. The gas pressurized bladder cooperates with the tubular piston rod to form an oil accumulator as the piston rod moves into the displacement chamber and progressively increases the pressure on the oil and piston rod as the angle of knee flexion increases. The bladder pressurized oil produces an upward biasing force on the piston rod to urge the leg to its extended position. An annular seal prevents the higher oil pressure in the displacement chamber from transferring to the operating chamber and the seal between the housing and the outer end portion of the piston rod and thereby significantly extends the service life of the control unit.

Other features and advantages of the invention will be apparent from the following description, the accompanying drawing and the appended claims.

BRIEF DESCRIPTION OF THE DRAWINGS

FIG. 1 is an elevational view of a prosthetic leg with a portion broken away to show the assembly of a hydraulic control unit constructed in accordance with the invention;

FIG. 2 is an axial section of the hydraulic control unit shown in FIG. 1 and enlarged about twice its normal size for showing detail construction of the unit;

FIG. 3 is a further enlarged section of an upper portion of the unit shown in FIG. 2;

FIG. 4 is a further enlarged section of an intermediate portion of the unit shown in FIG. 2; and FIG. 5 is a further enlarged section of an upper end portion of the unit shown in FIG. 2.

DESCRIPTION OF THE PREFERRED EMBODIMENT

FIG. 1 illustrates a prosthetic or artificial leg 10 which includes a bracket 11 secured to a cup-shaped socket portion 12 adapted to receive the thigh portion of an amputee's leg. The prosthetic leg 10 also includes a hollow lower leg portion 14 which projects upwardly from a foot portion 16 and is pivotally connected to the bracket 11 by a hinge pin 17 to form a knee joint 18. In accordance with the present invention, a hydraulic control unit 20 extends between the bracket 11 and the lower leg portion 14 and includes a machined aluminum cylinder or housing 22 which has an axis A and is pivotally connected to the lower leg portion 14 by a pair pivot pins 23 extending from the leg portion 14 into corresponding threaded bores 24 (FIG. 2) formed within outwardly projecting bosses 26 of the housing 22. The unit 20 also includes a tubular chrome plated steel piston rod 28 which projects from the housing 22 and is connected to the bracket 11 by a pivot pin 31. The pin 31 extends through a cross bore 32 (FIG. 2) formed within a titanium fitting 34 threaded into the outer end portion of the piston rod 28 and confining a resilient O-ring 36 to form a fluid-tight seal between the fitting 34 and outer end portion of the piston rod 28.

Referring to FIG. 2, the lower end portion of the housing 22 defines a hydraulic fluid or oil displacement chamber 42 which is closed by a bottom cap 43 threaded onto the lower end portion of the housing 22 and having a removable oil fill plug 44. The cap 43 is sealed to the housing by a resilient O-ring 46. The upper end portion of the housing 22 defines a cylindrical bore 47 which receives a cylindrical brass liner or sleeve by a resilient O-ring 46. The upper end portion of the housing 22 defines a cylindrical bore 47 which receives a cylindrical brass liner or sleeve 48 having a tapered or frusto-conical lower end surface 51 and an externally threaded upper end portion 52 which engages internal threads 53 formed within the upper end portion of the housing 22. The sleeve 48 is press-fitted with a brass liner or control bushing 55 which has a tapered frusto-conical lower end surface mating with the surface 51 and a tapered or frusto-conical upper end surface 58.

The control bushing 55 also has a staggered array of axially and circumferentially spaced flow control passages or ports 60 which extend through the bushing into corresponding circumferentially spaced and axially extending channels or passages 62 formed within the outer surface of the bushing. As a result of the tight fit of the control bushing 55 within the sleeve 48, each channel 62 forms an oil flow control passage which extends from a port 60 to either the lower tapered end surface 51 of the sleeve 48 or the upper tapered end surface 58 of the control bushing 55.

The tubular piston rod 28 has an inner end portion which projects into the housing 22 and includes an outwardly projecting flange 63 forming the inner end of the piston rod. The flange 63 normally engages an inwardly projecting flange 64 of the housing 22, and a resilient O-ring 65 is carried by the rod 28 adjacent the flange 63. An annular resilient seal 66 (FIG. 4) has an inverted U-shaped radial cross-section and encloses an annular spring with inverted V-shaped fingers 67. The seal 66 slidably engages the inner end portion of the piston rod 28, and an annular bearing 68 is threaded into the housing 22 and has a Teflon impregnated inner surface 69 to support the piston rod when it moves axially into the displacement chamber 42. The seal 66 is produced by Industrial Products Division of Shamban and sold under the trademark VARISEAL-M.

The piston rod 28 carries a cylindrical tight-fitting piston 70 (FIG. 2) which is made of a plastics material sold under the trademark TURCITE and retained on the rod 28 between a pair of thrust washers 72 located on the piston rod 28 by a pair of retaining rings 73. A resilient O-ring 77 restrains rotation of the sleeve 48, and an annular flexible one-way rubber valve 82 (FIG. 4) is retained within a counterbore formed within the lower end portion of the control bushing 55 between a mounting ring 83 and the upper surface of the bearing 68. The valve 82 forms a one way check valve which permits oil to flow only upwardly into an annular operating chamber 85 defined between the outer surface of the piston rod 28 and the inner surface of the control bushing 55.

Another annular valve 82 and support ring 83 (FIG. 3) are retained in a counterbore formed within the upper end portion of the bushing 55 and form a one way check valve which permits oil to flow only downwardly into the chamber 85. The upper annular valve 82 is retained within the counterbore by an annular collar 87 having an upper portion swagged or secured to an annular cover screw 90 having a lower end portion threaded into the housing 22 directly above the threaded upper end portion of the sleeve 48. The cover screw 90 is rotatable within the upper end portion of the housing 22, and a resilient O-ring 92 forms a fluid-tight seal between the screw 90 and housing 22 and restrains rotation of the screw 90.

A tapered or frusto-conical internal surface 94 (FIG. 3) is formed within the annular cover screw 90 and opposes the mating tapered surface 58 on the upper end portion of the bushing 55 to form therebetween an upper annular tapered flow passage or gap 96. A similar inner tapered or frusto-conical surface 97 (FIG. 4) is formed at the inner end of the bore 47 and cooperates with the opposing and mating tapered surface 51 to define a lower flow passage or gap 98. The upper gap 96 is adjustable between 0.0005 and 0.0015 inch by rotating the cover screw 90 with a surrounding cap 105 which is positively secured or staked to the cover screw. A limit pin or screw 107 is threaded into the cap 105 and projects into a notch or recess 109 which extends circumferentially approximately 330° around the end upper end portion of the housing 22 to limit rotation of the cap 105 and cover screw 90 through an angle of about 312°. The limit screw 107 also projects into a recess 111 which extends circumferentially approximately 180° within the upper end portion of an indicating ring 114 mounted for rotation on the upper end portion of the housing 22. A resilient O-ring 116 holds the indicating ring 114 on the housing 22 after the ring 114 is set.

A radial pin 118 (FIG. 2) projects from the cover screw 90 through a notch or recess extending circumferentially approximately 180° within the upper end portion of the control bushing 55. The inner end portion of the pin 118 is received within an annular recess formed within the top portion of the control bushing 55. Thus rotation of the cover screw 90 by the cap 105 is effective to rotate the assembly of the sleeve 48 and control bushing 55 and adjust the assembly axially within the bore 47 to adjust the bottom tapered gap 98 through a range of about 0.0005 to 0.0015 inch. The upper tapered gap 96 is then adjusted by rotation of the cover screw 90 with the cap 105 relative to the assembly of the sleeve and control bushing. The cover screw 90 retains an annular oil seal 121 (FIG. 3) which slidably engages the chromed outer surface of the piston rod 28. The seal 121 is constructed the same as the seal 66 and is retained by a backup washer and a set of Belville spring washers 124 and an annular metal ring 126 which is threaded into the cap 105 above the cover screw 90. A rubber wiper boot 127 is attached to the ring 126 and cleans the rod 28 during operation of the unit 20.

The upper internally threaded end portion of the piston rod 28 encloses a tubular fitting 132 (FIG. 2) which receives a Schrader-type valve 134 having a spring biased depressible valve stem 136. The fitting 132 projects into the upper end portion of an elongated rubber-like flexible bladder 140 which extends into the tubular piston rod 28 and has a closed dome-shaped lower end. The bladder 140 is molded with an upper end bead 138 (FIG. 5) which is pressed into an annular groove within the fitting 132 by a tapered sleeve 141 which mates with a tapered outer surface on the fitting 132 and forms a first fluid-tight seal. A resilient O-ring 142 also presses the bladder 140 into a groove 143 within the fitting 132 to form a second fluid-tight seal between the upper end portion of the bladder 140 and the piston rod 28. The bladder 140 is inflated through the valve 134 with a pressurized gas such as nitrogen when the fitting 34 is removed.

After the entire hydraulic control unit 20 is substantially assembled, the displacement chamber 42 is filled with a hydraulic fluid or oil by inverting the unit 20 and removing the plug 44. The operating chamber 85 is then filled with the hydraulic fluid or oil by removing the ring 126 and seal 121. After both chambers are completely filled and closed, the bladder 140 is inflated with a gas supplied through the Schrader valve 134 before the fitting 34 is assembled. The gas is pressurized so that a predetermined pressure is exerted on the oil within the displacement chamber 42 and the lower end portion of the piston rod 28. The pressurized oil exerts a force outwardly on the piston rod 28 to bias the rod to its normally extended position as shown in FIGS. 1 and 2 when the leg 10 is in its extended position. This variable biasing force exerted by the oil may be conveniently adjusted simply by changing the pressure of the gas within the bladder 140.

The hydraulic control unit 20 is installed within a prosthetic leg so that it spans the knee joint and the piston rod 28 is pushed into the housing 22 whenever the knee flexes or pivots on the cross pin 17. As the piston rod 28 moves inwardly, the rod is subjected to a changing hydraulic resistance or damping force by the piston 70 forcing oil outwardly through the control ports 60 located below the piston 70 and through the channels or passages 62. The oil displaced within chamber 42 by the piston rod 28 is forced upwardly into the piston rod 28 compressing and partially collapsing the bladder 140 so that the piston rod 28 and bladder 140 function as a pressurized oil accumulator. As the pressure of the gas within the bladder 140 increases with further flexing of the knee, the biasing force exerted by the oil against the piston rod 28 increases so that a greater biasing force is exerted on the lower leg portion 14 for moving it towards its extended position shown in FIG. 1.

As the piston 70 moves downwardly within the chamber 85, the oil forced outwardly from the chamber 85 through the ports 60 is forced upwardly within the corresponding channels 62, through the upper tapered restriction gap 96 and downwardly past the upper one way check valve 82 back into the operating chamber 85 above the piston 70. At the beginning of the compression stroke, all of the ports 60 and channels 62 serve as restricting fluid passages. However, as the piston 70 moves downwardly over the staggered holes or ports 60 in the control bushing 55, the number of ports 60 decreases thereby producing a higher resistance to oil flow and knee flexion as the angle of knee flexion increases. This is important for preventing excessive heal rise of the foot 16 throughout a wide range of walking speeds.

During extension of the piston rod 28 and the prosthetic leg 10, the process is reversed, and oil above the piston 70 within the operating chamber 85 flows outwardly through the control passages or ports 60 located above the piston 70, downwardly through the channels 62 which open into the lower tapered gap 98 and then back upwardly through the lower check valve 82 and into the chamber 85 below the piston 70. As in knee flexion, the number of control ports and channels 62 available for oil flow decreases as the piston moves upwardly and approaches the end of its motion or stroke. This upward movement of the piston to increasingly higher resistance is important in order to decelerate the leg movement and prevent an abrupt stop of the leg as it reaches its extended limit when the piston rod 28 is fully extended.

In addition to the damping force profile created by the staggered arrangement of the control ports 60, a constant damping force is created by restricting the oil flow through the upper and lower gaps 96 and 98, respectively. As mentioned above, the gaps are adjustable by turning the cap 105 which, in turn, adjusts the cover screw 90 and the control bushing axially 55 and sleeve 48 within the housing 22. This allows for independent adjustment of the upper and lower gaps and the resistance to knee flexion or extension, permitting each user to select the ideal set of resistances for his or her unique biomechanical needs.

From the drawing and the above description, it is apparent that a prosthetic leg having a knee joint equipped with a hydraulic control unit constructed in accordance with the invention, provides desirable features and advantages. For example, the construction of the hydraulic control unit 20 with the oil accumulator within the piston rod 28 provides for significantly reducing the size and weight of the unit, eliminates noise of operation and eliminates parts which wear. The unit 20 also provides for conveniently adjusting the pressure exerted by the hydraulic fluid or oil simply by adjusting the pressure of the gas within the bladder 140. In addition, the unit provides for conveniently adjusting the constant damping forces by independently adjusting the upper gap 96 and the lower gap 98.

The construction of the control unit 20 also provides for greater reliability, simplifies construction and manufacturing, and allows for greater part tolerances which provides for reducing the cost of the components assembled to form the unit 20. Also, the seal 66 (FIG. 4) prevents the continuous and usually higher oil pressure within the displacement chamber 42 from being transmitted to the operating chamber 85 and to the upper shaft seal 121. As a result, the seal 121 is exposed only to the dynamic oil pressure within the chamber 85 when the piston 70 is moving within the chamber 85 and no pressure when the piston 70 is not moving. Thus any leaking of oil past the seal 121 is substantially reduced or eliminated, and the unit 20 is provided with a significantly longer service life. Preferably, the flexible wall of the bladder 140 is always slightly collapsed so that there is no pressure loss across the bladder wall due to the elasticity of the bladder resisting stretching of the bladder. The means for attaching the upper end portion of the bladder to the piston rod 18 and the fitting 132, as shown in FIGS. 2 and 5, assures a positive fluid-tight seal for the gas within the bladder 140 and the oil surrounding the bladder. Also, as a result of the seal 66, the wear parts within the upper portion of the chamber 85 may be replaced or the oil may be replenished without disturbing the pressurized oil within the lower displacement chamber 42.

While the form of control unit 20 herein described constitutes a preferred embodiment of the invention, it is to be understood that the invention is not limited to this precise form of control unit, and that changes may be made therein without departing from the scope and spirit of the invention as defined in the appended claims.

The invention having thus been described, the following is claimed:

1. A hydraulic control unit in combination with a prosthetic leg assembly including an upper leg member for receiving the thigh portion of an amputee's leg and a lower leg member pivotally connected to the upper leg member, said unit extending between said upper and lower leg members for producing movement of the prosthetic leg assembly simulating that of the natural leg over a wide range of walking speeds, said unit comprising an elongated tubular housing having an axis, said housing including a first end portion including means defining a displacement chamber for receiving hydraulic fluid and a second end portion defining a bore, a flow control member disposed within said bore and defining an operating chamber for receiving hydraulic fluid, a piston rod having an inner portion extending into said displacement chamber and an outer portion projecting from said housing, a piston on said inner portion of said piston rod within said operating chamber, a supply of hydraulic fluid within each of said operating and displacement chambers, said fluid flowing within said flow control member and said operating chamber in response to axial movement of said piston and said piston rod within said operating chamber to effect damping of said piston rod, an accumulator for accumulating said fluid displaced within said displacement chamber when said piston rod moves into said housing and for maintaining a continuous static pressure on said piston rod for urging said piston rod outwardly from said housing, a first annular sealing member supported by said housing and engaging said piston rod for confining said fluid within said operating chamber, a second annular sealing member supported by said housing inwardly of said first sealing member and between said operating chamber and said displacement chamber, and said second sealing member having a resilient annular surface positively engaging said piston rod and configured to prevent the continuous hydraulic static pressure within said displacement chamber from transferring past said second sealing member to said operating chamber and to said first sealing member to avoid leakage of hydraulic fluid from said housing past said first sealing member for significantly extending the service life of said unit.

2. A control unit as defined in claim 1 where in said second sealing member comprises an annular channel-like body defining a cavity receiving said hydraulic fluid within said displacement chamber, and spring means within said cavity and cooperating with said hydraulic fluid to urge said body against said piston rod.

3. A control unit as defined in claim 1 wherein said first sealing member comprises an annular channel-like body defining a cavity receiving said hydraulic fluid within said operating chamber, and spring means within said cavity and cooperating with said hydraulic fluid to urge said body against said piston rod.

4. A control unit as defined in claim 1 and including a first removable plug member for filling said operating chamber with said hydraulic fluid, and a separate second removable plug member for filling said displacement chamber with said hydraulic fluid.

5. A control unit as defined in claim 1 and including an annular spring member surrounding said piston rod for holding said first sealing member against said hydraulic fluid within said operating chamber to accommodate adjustment of said flow control member and displacement of said hydraulic fluid within said operating chamber.

6. A control unit as defined in claim 1 wherein said piston comprises an annular body of rigid plastics material mounted on said piston rod, and a ring member for releasably retaining said body on said piston rod.

7. A control unit as defined in claim 1 wherein said piston rod is tubular and encloses a gas filled flexible bladder positioned to receive the pressure of said hydraulic fluid within said displacement chamber, and a fitting secured to said outer portion of said piston rod for retaining said bladder.

8. A control unit as defined in claim 7 and including mating tapered tubular members receiving therebetween an open end portion of said bladder, and said tubular members are enclosed within said outer portion of said piston rod.

9. A control unit as defined in claim 1 and including an annular bearing supported by said housing and surrounding said inner portion of said piston rod adjacent said second sealing member, and said bearing includes means forming a low friction surface engaging said piston rod.

10. A control unit as defined in claim 1 wherein said flow control member comprises a tubular sleeve slidably supported by said housing for axial adjustment, a control bushing disposed within said sleeve and defining said operating chamber, and said bushing and sleeve have means defining a series of flow control passages extending through said bushing from said operating chamber and axially between said bushing and said sleeve.

11. A hydraulic control unit in combination with a prosthetic leg assembly including an upper leg member for receiving the thigh portion of an amputee's leg and a lower leg member pivotally connected to the upper leg member, said unit extending between the upper and lower leg members for producing movement of the prosthetic leg assembly simulating that of the natural leg over a wide range of walking speeds, said unit comprising an elongated tubular housing having an axis, means for pivotally connecting said housing to one of said leg members, said housing including a first end portion including means defining a displacement chamber for receiving hydraulic fluid and a second end portion having a substantially cylindrical inner surface defining a bore, a tubular flow control member engaging said inner surface of said housing and defining an operating chamber for receiving hydraulic fluid, a piston rod having an inner portion extending into said displacement chamber and an outer portion projecting from said housing, means for pivotally connecting said outer portion of said piston rod to the other leg member, a piston on said inner portion of said piston rod within said operating chamber, a supply of hydraulic fluid within each of said operating and displacement chambers, said fluid flowing within said flow control member and said operating chamber in response to axial movement of said piston and said piston rod within said operating chamber to effect damping of said piston rod, an accumulator for accumulating said fluid displaced within said displacement chamber when said piston rod moves into said housing in response to pivoting of the leg members and for maintaining a continuous static pressure on said piston rod for urging said piston rod outwardly from said housing, a first annular sealing member supported by said housing and engaging said piston rod for confining said fluid within said operating chamber, a second annular sealing member supported by said housing inwardly of said first sealing member and engaging said piston rod between said operating chamber and said displacement chamber, and said second sealing member having a resilient annular surface positively engaging said piston rod and configured to prevent the continuous hydraulic static pressure within said displacement chamber from transferring past said second sealing member to said operating chamber and to said first sealing member to avoid leakage of hydraulic fluid from said housing past said first sealing member for significantly extending the service life of said unit.

12. A control unit as defined in claim 11 wherein said accumulator comprises a gas filled flexible bladder positioned to receive the pressure of said hydraulic fluid within said displacement chamber.

13. A control unit as defined in claim 12 wherein said piston rod is tubular and encloses said bladder, and a fitting secured to said outer portion of said piston rod for retaining said bladder within said piston rod.

14. A control unit as defined in claim 11 wherein said second sealing member comprises an annular channel-like body defining a cavity receiving said hydraulic fluid within said displacement chamber, and a spring member within said cavity and cooperating with said hydraulic fluid to urge said body against said piston rod.

15. A control unit as defined in claim 11 and including an annular spring member surrounding said piston rod for holding said first sealing member against said hydraulic fluid within said operating chamber to accommodate adjustment of said flow control member and displacement of said hydraulic fluid within said operating chamber.

16. A control unit as defined in claim 11 and including an annular bearing supported by said housing and surrounding said inner portion of said piston rod adjacent said second sealing member, and said bearing includes means forming a low friction surface engaging said piston rod.

17. A control unit as defined in claim 11 wherein said flow control member comprise a tubular sleeve slidably supported by said housing for axial adjustment, a control bushing disposed within said sleeve and defining said operating chamber, and said bushing and sleeve have means defining a series of flow control passages extending through said bushing from said operating chamber and axially between said bushing and said sleeve.

18. A hydraulic control unit in combination with a prosthetic leg assembly including an upper leg member for receiving the thigh portion of an amputee's leg and a lower leg member pivotally connected to the upper leg member, said unit extending between said upper and lower leg members for producing movement of the prosthetic leg assembly simulating that of the natural leg over a wide range of walking speeds, said unit comprising an elongated tubular housing having an axis, said housing including a first end portion defining a displacement chamber for receiving hydraulic fluid and a second end portion defining a bore, a flow control member disposed within said bore and defining an operating chamber for receiving hydraulic fluid, a tubular piston rod having an inner portion extending into said displacement chamber and an outer portion projecting from said housing, a piston on said inner portion of said piston rod within said operating chamber, a supply of hydraulic fluid within each of said operating and displacement chambers, said fluid flowing within said flow control member and said operating chamber in response to axial movement of said piston and said piston rod within said operating chamber to effect damping of said piston rod, a gas filled flexible bladder within said piston rod for accumulating said fluid displaced within said displacement chamber when said piston rod moves into said housing and for maintaining a continuous static pressure on said piston rod for urging said piston rod outwardly from said housing, a first annular sealing member supported by said housing and engaging said piston rod for confining said fluid within said operating chamber, a second annular sealing member supported by said housing inwardly of said first sealing member and between said operating chamber and said displacement chamber, and said second sealing member having a resilient annular surface positively engaging said piston rod and configured to prevent the continuous hydraulic static pressure within said displacement chamber from transferring past said second sealing member to said operating chamber and to said first sealing member to avoid leakage of hydraulic fluid from said housing past said first sealing member for significantly extending the service life of said unit.

* * * * *